United States Patent
Dai et al.

(10) Patent No.: US 7,417,069 B2
(45) Date of Patent: *Aug. 26, 2008

(54) HALOGENATED TRIPTOLIDE DERIVATIVES AS IMMUNOMODULATORS AND ANTICANCER AGENTS

(75) Inventors: Dongcheng Dai, Mountain View, CA (US); John H. Musser, San Carlos, CA (US)

(73) Assignee: Pharmagenesis, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/210,677

(22) Filed: Aug. 23, 2005

(65) Prior Publication Data

US 2005/0288364 A1 Dec. 29, 2005

Related U.S. Application Data

(62) Division of application No. 10/786,663, filed on Feb. 24, 2004, now Pat. No. 6,943,259.

(60) Provisional application No. 60/449,976, filed on Feb. 25, 2003.

(51) Int. Cl.
*A61K 31/36* (2006.01)
*C07D 493/14* (2006.01)

(52) U.S. Cl. ..................... 514/468; 549/297

(58) Field of Classification Search ............... 514/468, 514/885; 549/297
See application file for complete search history.

(56) References Cited

U.S. PATENT DOCUMENTS 5,430,054 A 7/1995 Qian et al.
6,150,539 A * 11/2000 Musser ............ 549/456

FOREIGN PATENT DOCUMENTS

| CN | 1052859 | 7/1991 |
| EP | 04 71 4219 | 9/2006 |
| WO | WO2005/000291 A1 | 1/2005 |
| WO | WO2005/020887 A2 | 3/2005 |

OTHER PUBLICATIONS

Pierre Viering et al Highly fluorinated amphiphiles 2001 pp. 337-354.*
Kirupa Shanmuganathan et al Enhanced brain delivery et al 1994 pp. 821-827.*
Drug design reviews Englebienne patrick et al The place of Bioisosteric Sila substitution in Drug design.*

* cited by examiner

*Primary Examiner*—Rita J Desai
(74) *Attorney, Agent, or Firm*—LeeAnn Gorthey; Susan T. Evans; Peter J. Dehlinger

(57) ABSTRACT

Compounds having the structure I:

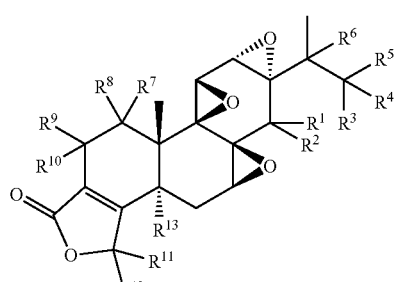

are useful for inducing cell death (apoptosis) and in immunosuppression. In structure I, $CR^1R^2$ is selected from CHOH, C=O, CHF, $CF_2$ and $C(CF_3)OH$;
$CR^6$ and $CR^{13}$ are selected from CH, COH and CF;
$CR^7R^8$, $CR^9R^{10}$ and $CR^{11}R^{12}$ are selected from $CH_2$, CHOH, C=O, CHF and $CF_2$; and
$CR^3R^4R^5$ is selected from $CH_3$, $CH_2OH$, C=O, COOH, $CH_2F$, $CHF_2$ and $CF_3$;
such that: at least one of $R^1$-$R^{13}$ comprises fluorine;
no more than two of $CR^3R^4R^5$, $CR^6$, $CR^7R^8$, $CR^9R^{10}$, $CR^{11}R^{12}$, and $CR^{13}$ comprises fluorine or oxygen;
and, when $CR^1R^2$ is CHOH, $CR^3R^4R^5$ is not $CH_2F$.

3 Claims, 3 Drawing Sheets

IL-2 Suppression

HALOGENATED TRIPTOLIDE DERIVATIVES AS IMMUNOMODULATORS AND ANTICANCER AGENTS

This application is a divisional of U.S. application Ser. No. 10/786.663 filed Feb. 24, 2004 now U.S. Pat. No. 6,943,259, which claims priority to U.S. Provisional Application Ser. No. 60/449,976, filed Feb. 25, 2003, both of which are incorporated herein by reference in their entirety.

FIELD OF THE INVENTION

The present invention relates to compounds useful as immunosuppressive, anti-inflammatory and anticancer agents.

REFERENCES

Gleichmann, E. et al., *Immunol. Today* 5:324 (1984).
He, Q. et al., *Beijing Da Xue Xue Bao* 35:252-5 (June 2003).
Jung, M. J. et al., U.S. Pat. No. 5,972,998 (1999).
Jung, M. J. et al., U.S. Pat. No. 6,004,999 (1999).
Korngold, R. and Sprent, J., *J. Exp. Med.* 148:1687 (1978).
Krishna, G. et al., *Am. J. of Pathology* 158(3):997-1004 (March 2001).
Kupchan, S. M. et al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al., *J. Chin. Pharm. Sci.* 1:12 (1992).
Murase, N. et al., *Transplantation* 55:701 (1993).
Ono and Lindsey, *J. Thor. Cardiovasc. Surg.* 57(2):225-29 (1969).
Panchagnula, R. and Thomas, N. S., *Intl J of Pharmaceutics* 201(2): 131-150 (2000).
Pu, L. et al., *Zhongguo Yaoli Xuebao* 11:76 (1990).
Qi, Y. et al., U.S. Pat. No. 5,663,335 (1997).
Qi, Y. et al., U.S. Pat. No. 5,962,516 (1999).
Qian, S. et al., U.S. Pat. No. 5,430,054 (1995).
Wang, J. and Morris, R. E., *Transplantation Proc.* 23:699 (1991).
Wang, X. et al., PCT Pubn. No. WO 2002/17931 (2002).
Wiedmann, T. et al., U.S. Pat. No. 5,843,452 (1998).
Zhou, Y. X. et al., *Ai Zheng* 21(10): 1108-8 (October 2002).

BACKGROUND OF THE INVENTION

Immunosuppressive agents are widely used in the treatment of autoimmune disease and in treating or preventing transplantation rejection, including the treatment of graft-versus-host disease (GVHD). Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD). Triptolide and certain derivatives and prodrugs thereof have also been reported to show anticancer activity. See, for example, Kupchan et al., 1972, 1977, as well as co-owned U.S. Pat. No. 6,620,843 (September 2003), which is hereby incorporated by reference.

In general, the biological activity per se of triptolide derivatives has been found to be less than that of native triptolide. However, these compounds often provide other benefits relative to native triptolide, in areas such as pharmacokinetics or biodistribution, by virtue of their activity as prodrugs and/or differences in lipid or aqueous solubility. See, for example, Jung et al., U.S. Pat. Nos. 5,972,998 and 6,004,999, Kupchan et al., U.S. Pat. No. 4,005,108, Lipsky et al., U.S. Pat. No. 5,294,443, and Qian et al., U.S. Pat. No. 5,430,054, as well as co-owned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), and references cited therein.

SUMMARY OF THE INVENTION

In one aspect, the invention provides compounds which are useful for immunosuppressive, anti-inflammatory and anticancer therapy. The compounds are derivatives of triptolide represented by Structure I:

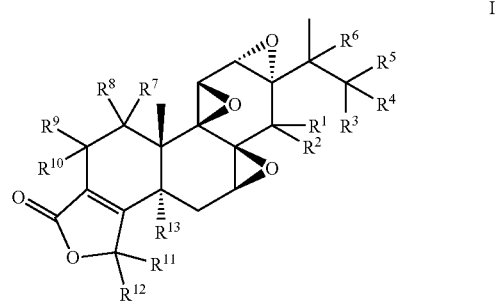

where:
$CR^1R^2$ is selected from CHOH, C=O, CHF, $CF_2$ and $C(CF_3)OH$;
$CR^6$ and $CR^{13}$ are selected from CH, COH and CF;
$CR^7R^8$, $CR^9R^{10}$ and $CR^{11}R^{12}$ are selected from $CH_2$, CHOH, C=O, CHF and $CF_2$; and
$CR^3R^4R^5$ is selected from $CH_3$, $CH_2OH$, C=O, COOH, $CH_2F$, $CHF_2$ and $CF_3$;
such that: at least one of $R^1$-$R^{13}$ comprises fluorine;
no more than two, and preferably no more than one, of $CR^3R^4R^5$, $CR^6$, $CR^7R^8$, $CR^9R^{10}$, $CR^{11}R^{12}$, and $CR^{13}$ comprises fluorine or oxygen;
and, when $CR^1R^2$ is CHOH, $CR^3R^4R^5$ is not $CH_2F$.

Preferably, the stereochemistry at $CR7R^8$ is such that, when $CR^7R^8$ is CHOH, it has a β-hydroxy configuration, and, when $CR^7R^8$ is CHF, it has an α-fluoro configuration. Similarly, the stereochemistry at $CR^9R^{10}$ is preferably such that, when $CR^9R^{10}$ is CHOH, it has a β-hydroxy configuration, and, when $CR^9R^{10}$ is CHF, it has an α-fluoro configuration.

In preferred embodiments of structure I, $CR^1R^2$ is CHF, having an α-fluoro configuration.

Preferred embodiments also include compounds in which exactly one carbon center selected from $CR^1R^2$, $CR^3R^4R^5$, $CR^6$, $CR^7R^8$, $CR^9R^{10}$, and $CR^{11}R^{12}$ comprises fluorine. More preferably, exactly one of $CR^1R^2$, $CR^6$, $CR^7R^8$, $CR^9R^{10}$, and $CR^{11}R^{12}$ comprises fluorine.

In selected embodiments, only $CR^1R^2$ comprises fluorine. Accordingly, in these embodiments, $CR^1R^2$ is selected from $CF_2$, CHF, and $C(CF_3)OH$. The stereochemistry at $CR^1R^2$ is preferably such that, when $CR^1R^2$ is $C(CF_3)OH$, it has a β-hydroxy configuration, and, when $CR^1R^2$ is CHF, it has an α-fluoro configuration.

In other selected embodiments of structure I, either $CR^9R^{10}$ or $CR^3R^4R^5$ comprises fluorine, and $CR^1R^2$ comprises oxygen; preferably, $CR^1R^2$ is C=O or, more preferably, CHOH (β-hydroxy). In these embodiments, for example, $CR^9R^{10}$ is selected from $CF_2$ and CHF (preferably α-fluoro), or $CR^3R^4R^5$ is selected from $CHF_2$ or $CF_3$.

In further selected embodiments of structure I, either $CR^7R^8$ or $CR^{11}R^{12}$ comprises fluorine, and $CR^1R^2$ comprises oxygen; preferably, $CR^1R^2$ is C=O or, more preferably, CHOH(β-hydroxy). In these embodiments, for example, $CR^7R^8$ is selected from $CF_2$ and CHF (preferably α-fluoro), or $CR^{11}R^{12}$ is selected from $CF_2$ and CHF.

In other aspects, the invention provides a method of effecting immunosuppression, and a method of inducing apoptosis in a cell, which is useful in antiproliferative therapy, especially anticancer therapy. The methods comprise administering to a subject in need of such treatment, or contacting said cell, respectively, with an effective amount of a compound having the structure I as described herein. Alternatively, the invention encompasses the use of a compound of structure I for preparation of a medicament for effecting immunosuppression or for inducing apoptosis in a cell. The compound is typically provided in a pharmaceutically acceptable carrier. Specific embodiments of the methods and uses may employ any of the specific embodiments of structure I described herein.

These and other objects and features of the invention will become more fully apparent when the following detailed description of the invention is read in conjunction with the accompanying drawings.

DETAILED DESCRIPTION OF THE INVENTION

I. Triptolide Derivatives

Figure 1:
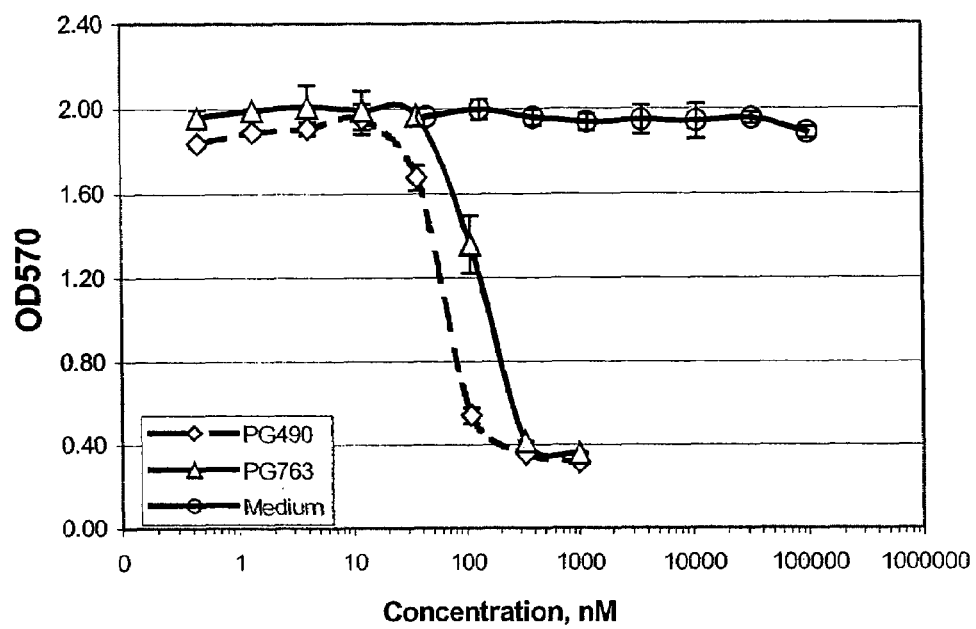
FIG. 1 shows the cytotoxic effect in Jurkat cells of a compound of the invention, 14-deoxy-14α-fluorotriptolide (designated PG763), in comparison with triptolide (designated PG490) (Example 2)

For the purposes of the current disclosure, the following numbering scheme is used for triptolide and triptolide derivatives:

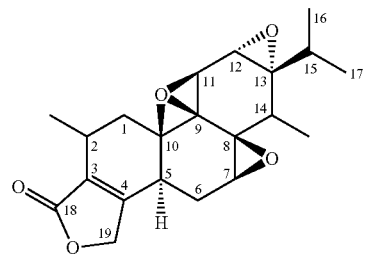

The compounds of the invention are derivatives of triptolide resulting from substitution of one or more hydroxyl or hydrogen atoms, at C1, C2, C5, C14, C15, C16, and/or C19, preferably at C2, C14, or C16, with a halogen atom, preferably chlorine or fluorine, and most preferably fluorine, as described further herein. More specifically, the compounds of the invention are represented by Structure I below:

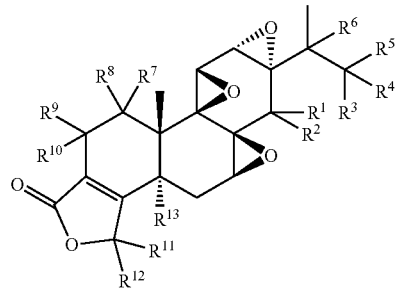

where:
$CR^1R^2$ is selected from CHOH, C=O, CHF, $CF_2$ and $C(CF_3)OH$;
$CR^6$ and $CR^{13}$ are selected from CH, COH and CF;
$CR^7R^8$, $CR^9R^{10}$ and $CR^{11}R^{12}$ are selected from $CH_2$, CHOH, C=O, CHF and $CF_2$; and
$CR^3R^4R^5$ is selected from $CH_3$, $CH_2OH$, C=O, COOH, $CH_2F$, $CHF_2$ and $CF_3$;
such that at least one of $R^1$-$R^{13}$ comprises fluorine;
no more than two, and preferably no more than one, of $CR^3R^4R^5$, $CR^6$, $CR^7R^8$, $CR^9R^{10}$, $CR^{11}R^{12}$, and $CR^{13}$ comprises fluorine or oxygen;
and, when $CR^1R^2$ is CHOH, $CR^3R^4R^5$ is not $CH_2F$.

Preferably, the stereochemistry at each of $CR^7R^8$ and $CR^9R^{10}$ is such that CHOH has a β-hydroxy configuration and CHF has an α-fluoro configuration.

In preferred embodiments of structure I, $CR^1R^2$ is CHF(α). (As used herein, the notation "CHX(α)" or "CHX(β)" indicates that the non-hydrogen substituent, X, has the α or the β configuration, respectively.) More preferably, in these embodiments, only $CR^1R^2$ comprises fluorine. Still more preferably, in these embodiments, only $CR^9R^{10}$ and/or $CR^3R^4R^5$ comprises oxygen; e.g. one or both, preferably one, of $CR^9R^{10}$ and/or $CR^3R^4R^5$ is CHOH (preferably CHOH(β) for $CR^9R^{10}$). Alternatively, in these embodiments, none of $CR^3R^4R^5$, $CR^6$, $CR^7R^8$, $CR^9R^{10}$, $CR^{11}R^{12}$, and $CR^{13}$ comprises oxygen.

Preferred embodiments of structure I also include compounds in which exactly one carbon center selected from $CR^1R^2$, $CR^3R^4R^5$, $CR^6$, $CR^7R^8$, $CR^9R^{10}$, and $CR^{11}R^{12}$ comprises fluorine. More preferably, exactly one of $CR^1R^2$, $CR^7R^8$, $CR^9R^{10}$, and $CR^{11}R^{12}$ comprises fluorine. Preferably, in these embodiments, only $CR^9R^{10}$ and/or $CR^3R^4R^5$ comprises oxygen; e.g. one or both, preferably one, of $CR^9R^{10}$ and/or $CR^3R^4R^5$ is CHOH (preferably CHOH(β) for $CR^9R^{10}$). Alternatively, in these embodiments, none of $CR^3R^4R^5$, $CR^6$, $CR^7R^8$, $CR^9R^{10}$, $CR^{11}R^{12}$, and $CR^{13}$ comprises oxygen.

In selected embodiments of structure I, only $CR^1R^2$ comprises fluorine. Accordingly, $CR^1R^2$ is selected from $CF_2$, CHF, and $C(CF_3)OH$. The stereochemistry at $CR^1R^2$ is preferably such that $C(CF_3)OH$ is $C(\alpha-CF_3)\beta-OH$, or CHF is $CH(\alpha-F)$.

In other selected embodiments of structure I, either $CR^9R^{10}$ or $CR^3R^4R^5$ comprises fluorine and $CR^1R^2$ comprises oxygen; preferably, $CR^1R^2$ is C=O or, more preferably, CHOH (β-hydroxy). In these embodiments, $CR^9R^{10}$ is $CF_2$ or CHF (preferably α-fluoro), and $CR^3R^4R^5$ is preferably $CHF_2$ or $CF_3$.

In further selected embodiments of structure I, either $CR^7R^8$ or $CR^{11}R^{12}$ comprises fluorine and $CR^1R^2$ comprises oxygen; preferably, $CR^1R^2$ is C=O or, more preferably, CHOH(β-hydroxy). In these embodiments, $CR^7R^8$ is $CF_2$ or CHF (preferably α-fluoro), and $CR^{11}R$ is $CF_2$ or CHF.

The invention also includes compounds analogous to those of structure I where fluorine is replaced with a different halogen atom, i.e. chlorine, bromine, or iodine, particularly chlorine; e.g. 14-deoxy-14α-chloro triptolide. Other selected and preferred embodiments of such compounds correspond to those described for fluorinated compounds of structure I, above.

A. Preparation

The compounds of the invention may be prepared from triptolide or its hydroxylated derivatives. The latter compounds include tripdiolide (2-hydroxytriptolide) or 16-hydroxytriptolide, which, along with triptolide, can be obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for obtaining triptolide, tripdiolide and 16-hydroxytriptolide are known in the art and are described, for example, in Kupchan et al. (1972, 1977); Lipsky et al. (1994); Pu et al. (1990); and Ma et al. (1992).

The 5-hydroxy derivative of triptolide can be prepared by selenium dioxide oxidation of triptolide, as described in co-owned U.S. provisional application Ser. No. 60/532,702. Briefly, in a typical preparation, a solution of triptolide and about 2.2 equivalents of selenium dioxide in dioxane is stirred at about 90° C. under $N_2$ for 72 hrs.

Incubation of triptolide with *Cunninghamella blakesleana*, as described by L. Ning et al. (*Tetrahedron* 59(23):4209-4213, 2003), produces the above hydroxylated derivatives as well as 1β-hydroxytriptolide, triptolidenol (15-hydroxytriptolide), 19α-hydroxytriptolide, and 19β-hydroxytriptolide. The products are isolated by standard procedures; i.e. extraction of the filtered culture broth with ethyl acetate, concentration, and silica gel chromatography of the residue.

Compounds of Structure I can be prepared from triptolide, its hydroxylated derivatives, or oxidized derivatives thereof, by reaction of a hydroxyl or oxo group at C1, C2, C5, C14, C15, C16, and/or C19 with a fluorinating agent, forming a CHF or $CF_2$ group, respectively, at said carbon.

Description of such fluorinating reagents is provided in references such as *Chemistry of Organic Fluorine Compounds II* (editors M. Hudlicky and A. E. Pavlath; ACS Monograph 187, 1995) and *Organofluorine Chemistry: Principles and Commercial Applications* (editors R. E. Banks, B. E. Smart and J. C. Tatlow; Plenum Press, 1994). For example, reagents suitable for conversion of a hydroxyl group (C—OH) to C—F include HF-amine complexes, such as HF-pyridine (Olah's reagent) or HF-2,4,6-collidine, sulfur tetrafluoride ($SF_4$) and various $SF_4$ derivatives, including (diethylamino)sulfur trifluoride (DAST), (dimethylamino)sulfur trifluoride (methyl-DAST), morpholino sulfur trifluoride (morph-DAST), and [bis(2-methoxyethyl)amino]sulfur trifluoride (Deoxo-Fluor™). The hydroxyl group may first be converted to a leaving group, such as triflate, which is then displaced with a nucleophilic fluoride reagent, such as tris (dimethylamino)sulfur (trimethylsilyl)difluoride (TAS-F), tetra-n-butylammonium difluorotriphenylsilicate, or inorganic salts, such as KF, CsF and $Bu_4NF$. These reactions generally proceed with inversion of stereochemistry, as illustrated below.

For example, native triptolide, having a β-hydroxyl at C14, can be converted to 14-deoxy-14-α-fluorotriptolide (designated herein as PG763) by reaction with DAST, as described in Example 1. Alternatively, epitriptolide (14-α triptolide, designated herein as comparative compound PG524) can be used to prepare 14-deoxy-14-β-fluorotriptolide.

Tripdiolide (having β-hydroxyls at C14 and C2) can be similarly converted to 14-deoxy-2α, 14α-difluorotriptolide. The compound may be obtained as a mixture with 2α-fluorotriptolide if a limiting amount of fluorinating reagent is used (see below).

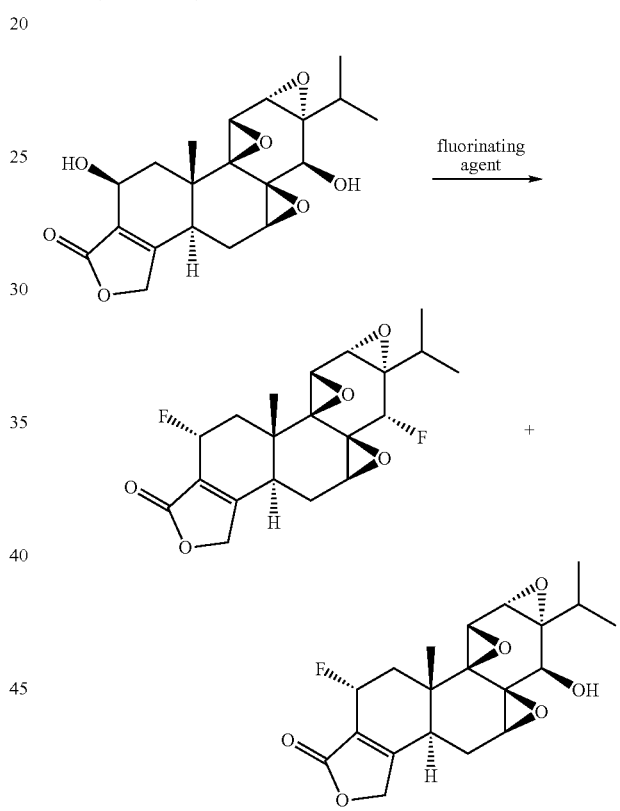

Reaction of 16-hydroxytriptolide with a stoichiometric or excess amount of fluorinating agent provides 14-deoxy-14α, 16-difluorotriptolide, as shown below.

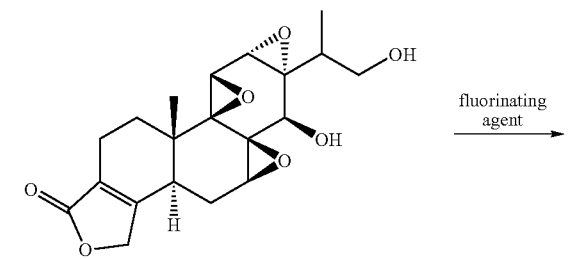

-continued

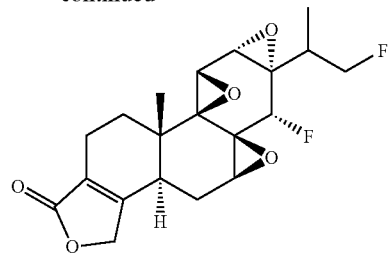

Sulfur tetrafluoride and derivatives thereof, e.g. those listed above, are also the most frequently used fluorinating agents used to convert oxo groups (e.g. aldehydes or ketones) to gem-difluorides. Also suitable is 2,2-difluoro-1,3-dimethylimidazolidine (DFI).

An oxo group at C2, C14 and/or C16 of triptolide can be formed by oxidation of one or more hydroxyl groups to keto or aldehyde groups. Description of oxidizing reagents and processes suitable for selective oxidation of alcohols is provided in references such as M. Hudlicky, *Oxidations in Organic Chemistry* (ACS Monograph Series 186, 1990), R. C. Larock, *Comprehensive Organic Transformations* ($2^{nd}$ Ed., Wiley, 1999), or J. March, *Advanced Organic Chemistry* ($4^{th}$ Ed., Wiley, 1992). Strong acidic or basic conditions should be avoided. If necessary, the desired product is isolated from any side products using, for example, HPLC.

For example, the secondary alcohol at C14 of triptolide can be oxidized to a ketone (giving the compounds known as triptonide) using, for example, chromium trioxide-pyridine complex, $CrO_2Cl_2$/alumina, or comparable oxidizing reagents. Reaction with, for example, DAST gives 14-deoxy-14,14-difluorotriptolide, as shown below.

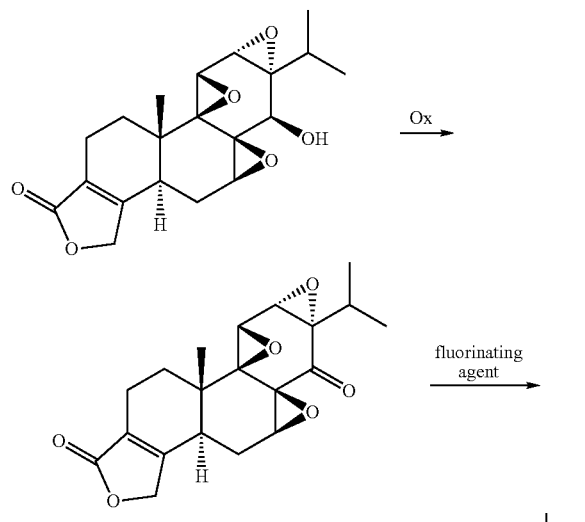

Both secondary alcohols of tripdiolide (2-hydroxy triptolide) can also be oxidized to ketones using such oxidants. Reaction with DAST or another suitable reagent gives the tetrafluoro compound shown below. When the reagent is used in a limiting amount, the 2,2-difluorocompound may also be obtained, as shown.

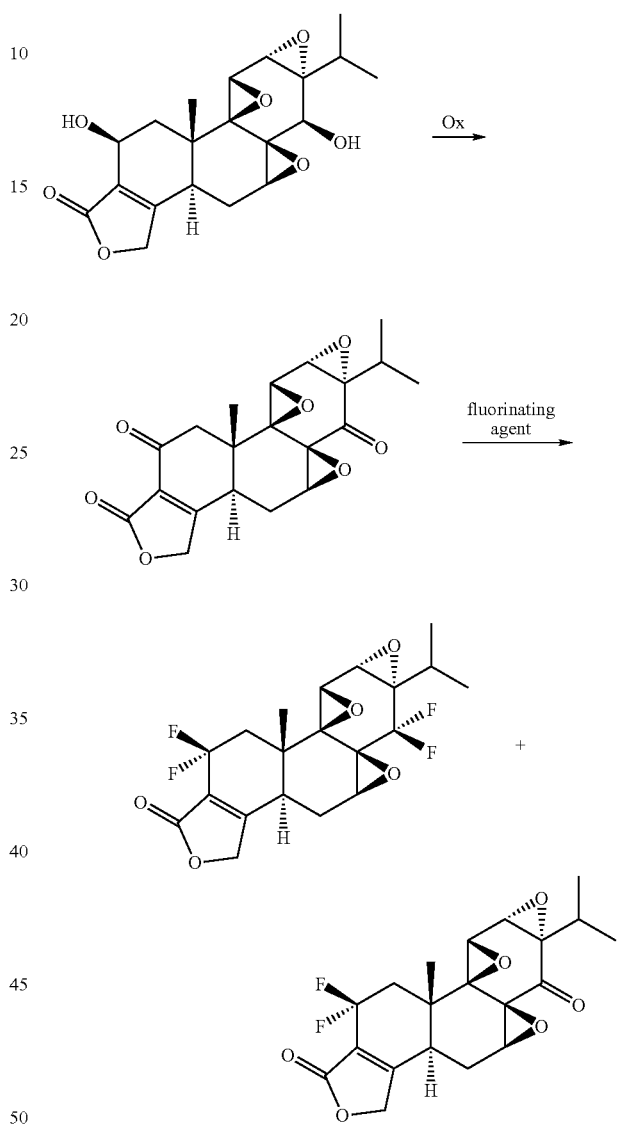

Alternatively, the less hindered alcohol at C2 of tripdiolide can be selectively oxidized to the ketone, using a stoichiometric amount of an oxidizing reagent such as those noted above, under mild conditions.

For oxidation of both the secondary and primary alcohols of 16-hydroxy triptolide, one preferably employs a reagent that will not further oxidize the product aldehyde, e.g. DMSO, pyridinium chlorochromate (Corey' reagent), or ceric ammonium nitrate, to give the keto-aldehyde intermediate. Reaction of the keto aldehyde with DAST or another suitable reagent gives the tetrafluoro compound shown below. Again, when the fluorinating reagent is used in a limiting amount, the 14-oxo-16,16-difluorocompound may also be obtained, as shown.

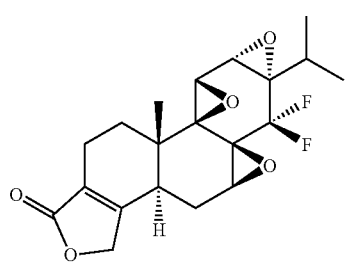

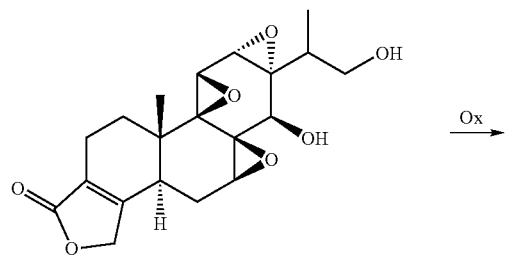

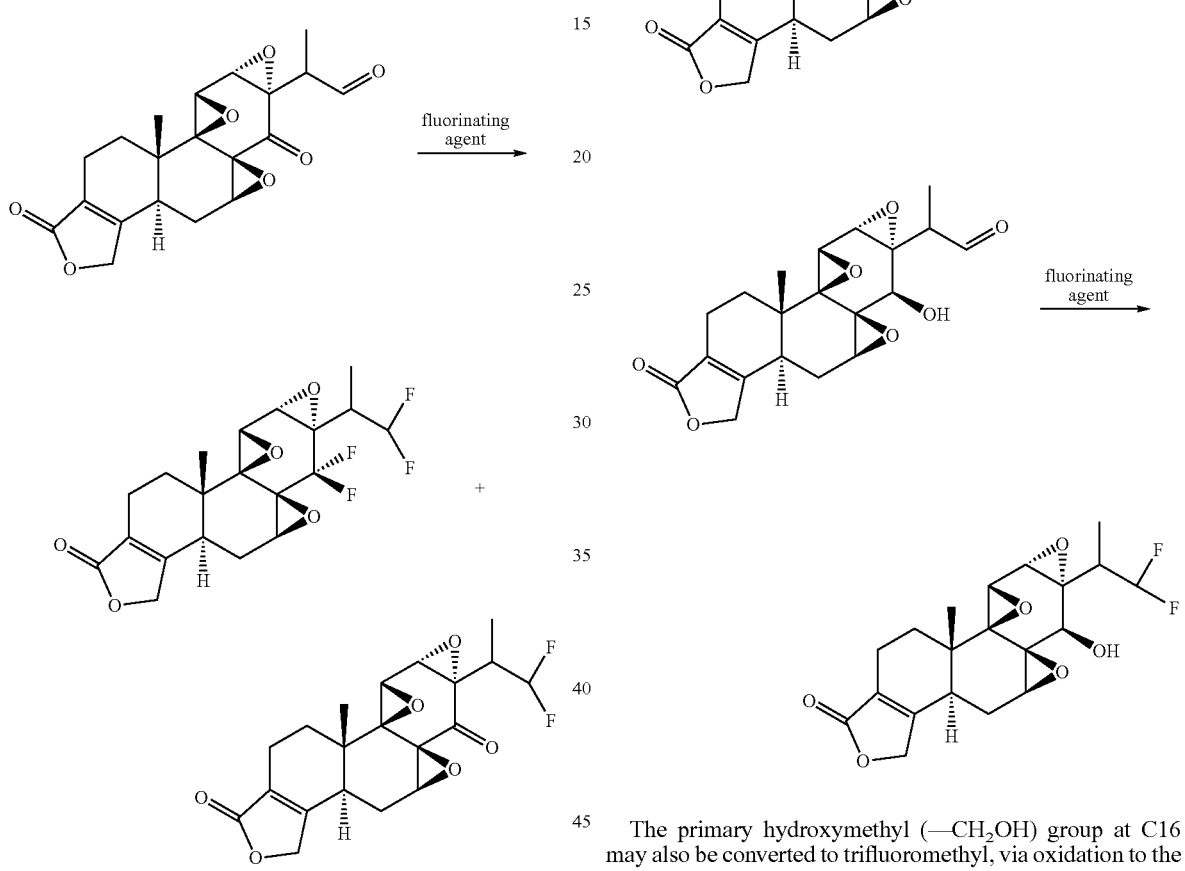

The primary alcohol of 16-hydroxy triptolide can also be oxidized selectively, using a reagent such as, for example, $RuCl_2(PPh_3)_3$; $(Me_3SiO)_2$/catalytic $RuCl_2(PPh_3)_3$; DMSO/ClCOCOCl/$Et_3N$; or DMSO/pyridine.$SO_3$/$i$-$Pr_2NEt$ (see Larock, cited above). The aldehyde can then be converted to 16,16-difluorotriptolide, as shown below.

The primary hydroxymethyl (—$CH_2OH$) group at C16 may also be converted to trifluoromethyl, via oxidation to the carboxylic acid followed by reaction with $SF_4$, as shown in the scheme below:

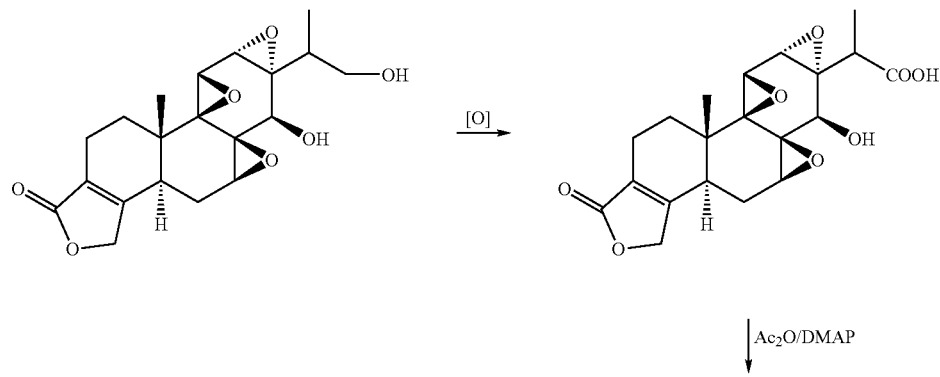

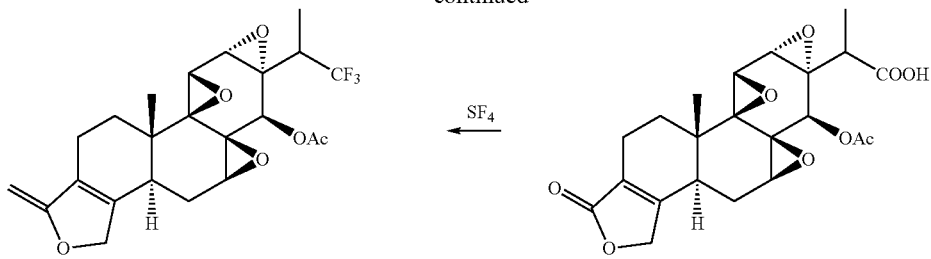

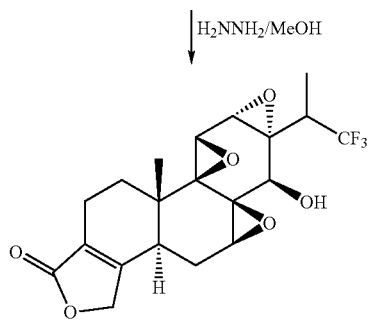

A trifluoromethyl group may be introduced at C14, or at another center bearing a secondary or primary hydroxyl, e.g. C1, C2, C16, or C19, by oxidation to the ketone, followed by reaction with trifluoromethyl trimethylsilane, as shown in the scheme below:

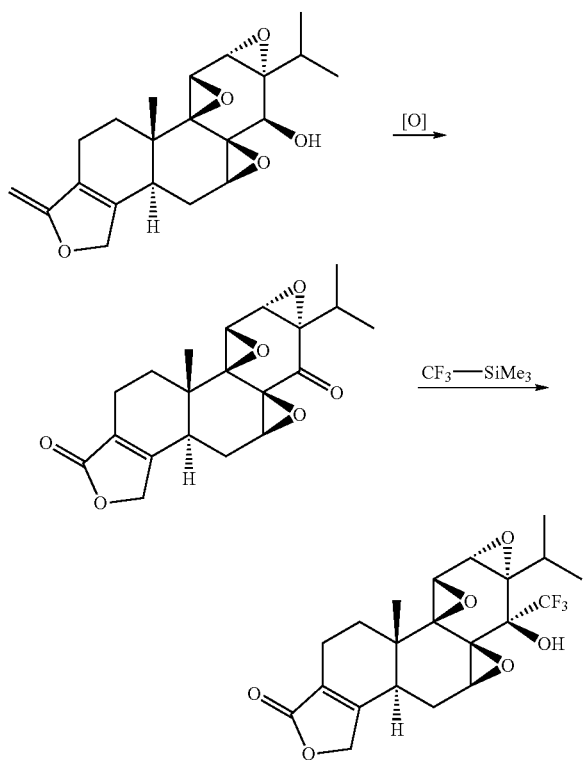

Preparation of analogous compounds in which fluorine is replaced with a different halogen atom can generally be prepared by analogous methods. Methods for converting C—OH to C—X, where X is Cl, Br, or I, are well known in the art. Reagents for preparation of chlorides, for example, include $SOCl_2$ or $PCl_5$, $POCl_3$, etc. Again, conversion of hydroxyl to a leaving group such as tosylate or triflate, followed by reaction with a halide reagent, is a recommended route. See, for example, Larock, *Comprehensive Organic Transformations* (VCH, New York, 1989), p. 360. $PCl_5$ can also be used in an analogous manner to $SF_4$ to form gem-dichlorides from aldehydes or ketones.

B. Biological Activity

As described above, various derivatives and analogs of triptolide are known in the art, and many are therapeutically useful. These compounds often provide benefits relative to native triptolide in areas such as pharmacokinetics or biodistribution, by virtue of their activity as prodrugs and/or changes in lipid or aqueous solubility. However, in general, the biological activity per se of such derivatives and analogs has been found to be less than native triptolide.

Figure 2:
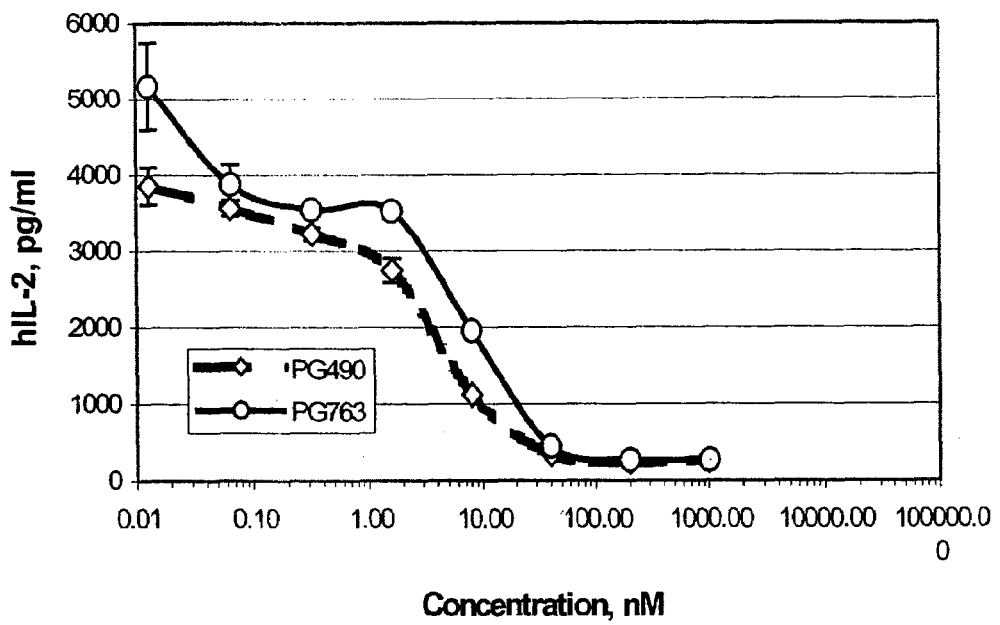
FIG. 2 shows inhibition of IL-2 production in Jurkat cells by a compound of the invention (PG763), in comparison with triptolide (Example 4)
Figure 3A:
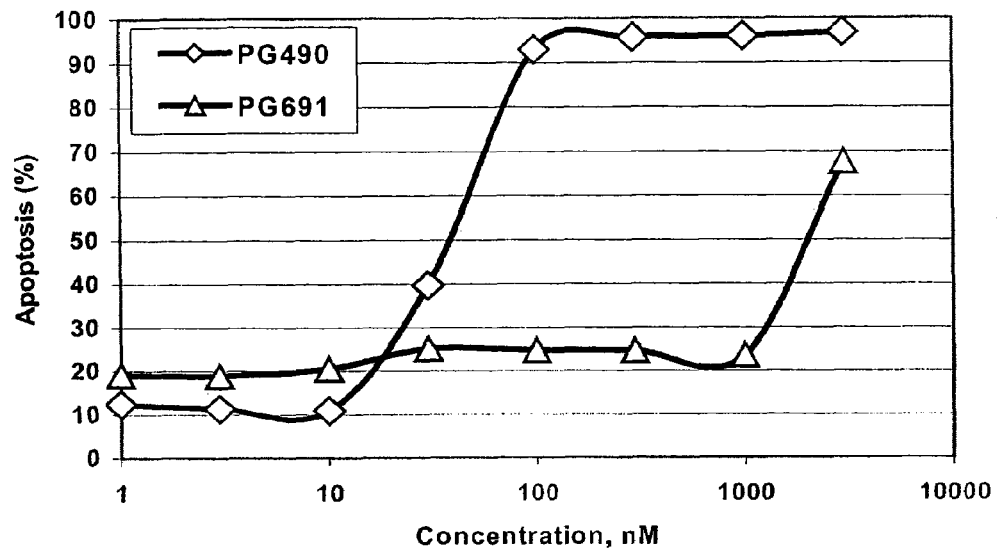
FIGS. 3A-B shows dose-dependent induction of apoptosis in Jurkat cells by comparative compounds, 14-α-hydroxytriptolide (also referred to as epitriptolide; designated PG524) and 14-β-(methylthio)methyl triptolide (designated PG691), in comparison with triptolide (Example 3)
Figure 3B:
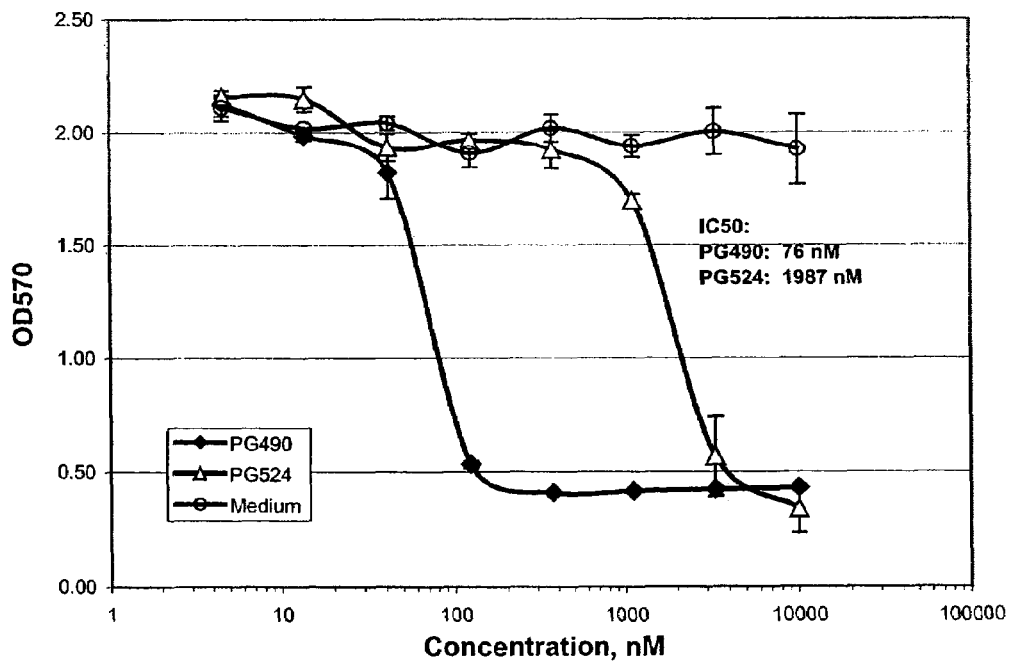
Figure 4A:
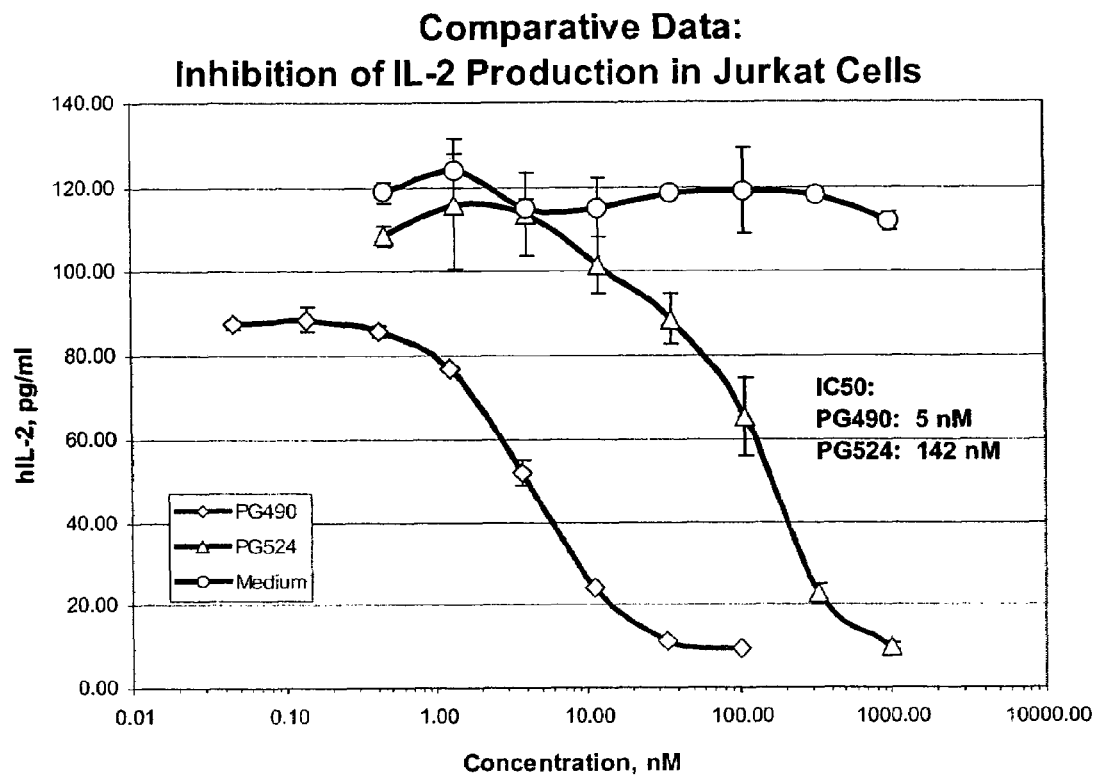
FIGS. 4A-B show inhibition of IL-2 production in Jurkat cells by comparative compounds, 14-α-hydroxytriptolide (also referred to as epitriptolide) and 14-β-(methylthio)methyl triptolide, in comparison with triptolide (Example 4).
Figure 4B:
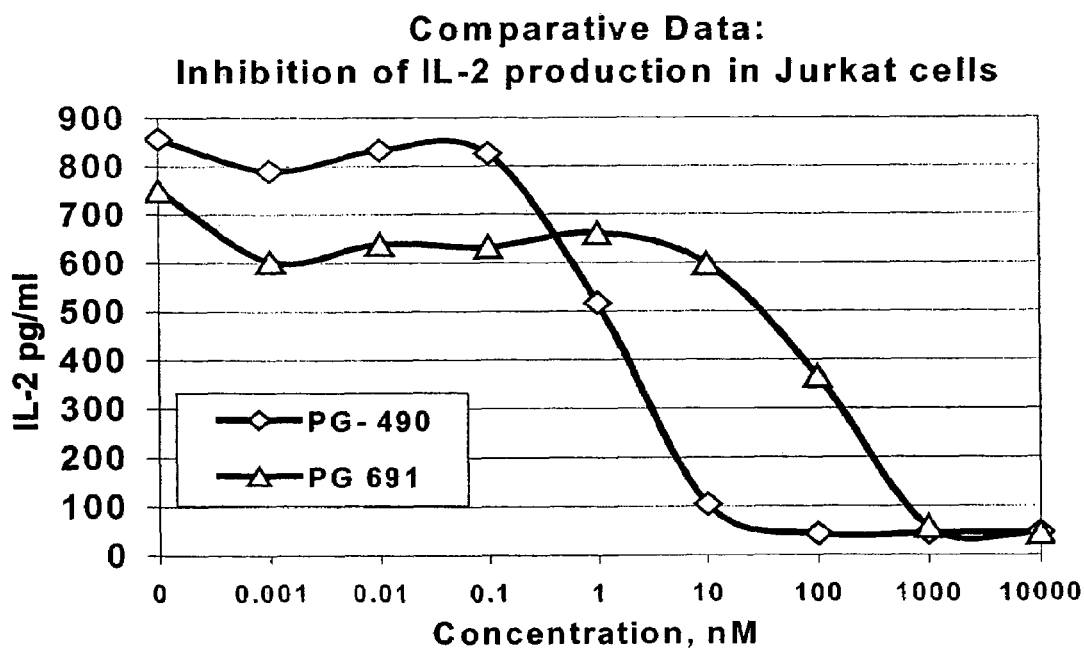

In particular, it has generally been regarded in the art that the presence of a hydrogen donor group at the 14 position, and preferably the 14β position, is key to maintaining bioactivity in triptolide derivatives. See, for example, the comparative data in FIGS. 3A-B and 4A-B herein. As shown in FIGS. 3A and 4A, epitriptolide, having the α-hydroxy stereochemistry at C14, while having immunosuppressive and apoptotic activity, was significantly less active than triptolide (approximately 30 fold less potent in the immunosuppression assay and 25 fold less potent in the apoptosis assay). In a compound having 14β stereochemistry and electronegative substituents, but not a hydrogen donor group, at C14, i.e. 14β-(methylthio) methyl triptolide, a greater reduction in bioactivity, relative to triptolide, was seen (FIGS. 3B and 4B) (approximately 60 fold less potent than triptolide in the immunosuppression assay and 40 fold less potent in the apoptosis assay). Accordingly, the very high bioactivity of a 14-deoxy-14α-fluoro compound of the invention (PG763) is surprising in view of the state of the art, since the compound lacks a hydrogen donor group at the 14 position. As shown in FIGS. 1-2, the activity of PG763 in assays evaluating cytotoxicity and IL-2 inhibition was nearly equivalent to that of triptolide.

Accordingly, 14-deoxy-14α-fluoro compounds are particularly preferred embodiments of structure I as disclosed herein. In a specific embodiment, the compound is PG763.

II. Therapeutic Compositions

Formulations containing the triptolide derivatives of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of nontoxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide derivative in a suitable intravenous solution, such as sterile physiological salt solution.

Liquid compositions can be prepared by dissolving or dispersing the triptolide derivative (about 0.5% to about 20%) and optional pharmaceutical adjuvants in a pharmaceutically acceptable carrier, such as, for example, aqueous saline, aqueous dextrose, glycerol, or ethanol, to form a solution or suspension.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in an effective amount for effecting immunosuppression in a subject or apoptosis in a targeted cell.

As described, for example, in Panchagnula et al. (2000), the partition coefficient or logP of a pharmaceutical agent can affect its suitability for various routes of administration, including oral bioavailability. The compounds described herein, by virtue of substitution of fluorine for one or more hydroxyl groups, are expected to have higher calculated logP values than the parent compound, triptolide, making them better candidates for oral availability.

III. Immunomodulating and Antiinflammatory Treatment

As shown in FIG. 2, a compound of structure I, 14-deoxy-14α-fluorotriptolide (designated PG763), inhibited IL-2 production in Jurkat cells (see Example 4) in a dose-dependent manner, at concentrations comparable to those in similar assay using triptolide. The invention thus includes the use of the invention compounds as immunosuppressive agents, e.g. as an adjunct to transplant procedures or in treatment of autoimmune disease.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow transplant or other transplant of hematopoietic stem cells from a donor tissue source containing mature lymphocytes, the transferred lymphocytes recognize the host tissue antigens as foreign. These cells become activated and mount an attack upon the host (a graft-versus-host response) that can be life-threatening. Moreover, following an organ transplant, the host lymphocytes recognize the foreign tissue antigens of the organ graft and mount cellular and antibody-mediated immune responses (a host-versus-graft response) that lead to graft damage and rejection.

One result of an autoimmune or a rejection reaction is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off Indeed, patients treated with such nonspecific immunosuppressive agents are as likely to succumb from infection as they are from their autoimmune disease.

The compositions of the present invention are useful in applications for which triptolide and its prodrugs and other derivatives have proven effective, e.g. in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. Triptolide and the present derivatives are also useful for treatment of other inflammatory conditions, such as traumatic inflammation, and in reducing male fertility.

The compositions are useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The compositions are also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosis (SLE), lupus nephritis, multiple sclerosis, myasthenia gravis, psoriasis, primary biliary cirrhosis, rheumatoid arthritis and uveitis, asthma, atherosclerosis, Hashimoto's thyroiditis, allergic encephalomyelitis, glomerulonephritis, and various allergies.

Further uses may include the treatment and prophylaxis of inflammatory and hyperproliferative skin diseases and cutaneous manifestations of immunologically mediated illnesses, such as psoriasis, atopic dermatitis, pemphigus, urticaria, cutaneous eosinophilias, acne, and alopecia areata; various eye diseases such as conjunctivitis, uveitis, keratitis, and sarcoidosis; inflammation of mucous and blood vessels such as gastric ulcers, vascular damage caused by ischemic diseases and thrombosis, ischemic bowel diseases, inflammatory bowel diseases, and necrotizing enterocolitis; intestinal inflammations/allergies such as Coeliac diseases and ulcerative colitis; renal diseases such as interstitial nephritis, Good-pasture's syndrome, hemolytic-uremic syndrome and diabetic nephropathy; hematopoietic diseases such as idiopathic thrombocytopenia purpura and autoimmune hemolytic anemia; skin diseases such as dermatomyositis and cutaneous T cell lymphoma; circulatory diseases such as arteriosclerosis and atherosclerosis; renal diseases such as ischemic acute renal insufficiency and chronic renal insufficiency; and Behcet's disease.

The compositions and method of the invention are also useful for the treatment of inflammatory conditions such as asthma, both intrinsic and extrinsic manifestations, for example, bronchial asthma, allergic asthma, intrinsic asthma, extrinsic asthma and dust asthma, particularly chronic or inveterate asthma (for example, late asthma and airway hyperresponsiveness). The composition and method may also be used for treatment of other inflammatory conditions, including traumatic inflammation, inflammation in Lyme disease, chronic bronchitis (chronic infective lung disease), chronic sinusitis, sepsis associated acute respiratory distress syndrome, and pulmonary sarcoidosis. For treatment of respiratory conditions such as asthma, the composition is preferably administered via inhalation, but any conventional route of administration may be useful.

In treating an autoimmune condition, the patient is given the composition on a periodic basis, e.g., 1-2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient. The dose that is administered is preferably in the range of 1-25 mg/kg patient body weight per day, with lower amounts being preferred for parenteral administration, and higher amounts being preferred for oral administration. Optimum dosages can be determined by routine experimentation according to methods known in the art.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1-25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

In treatment or prevention of graft-versus-host disease, resulting from transplantation into a recipient of matched or mismatched bone marrow, spleen cells, fetal tissue, cord blood, or mobilized or otherwise harvested stem cells, the dose is preferably in the range 0.25-2 mg/kg body weight/day, preferably 0.5-1 mg/kg/day, given orally or parenterally.

Also within the scope of the invention is a combination therapy comprising a compound of structure I and one or more conventional immunosuppressive agents. These immunosuppressant agents within the scope of this invention include, but are not limited to, IMUREK™ (azathioprine sodium), brequinar sodium, SPANIDIN™ (gusperimus trihydrochloride, also known as deoxyspergualin), mizoribine (also known as bredinin), CELLCEPT™ (mycophenolate mofetil), NEORAL™ (Cyclosporin A; also marketed as a different formulation under the trademark SANDIMMUNE™) PROGRAF™ (tacrolimus, also known as FK-506), RAPIMMUNE™ (sirolimus, also known as rapamycin), leflunomide (also known as HWA-486), ZENAPAX™, glucocorticoids, such as prednisolone and its derivatives, antibodies such as orthoclone (OKT3), and antithymyocyte globulins, such as thymoglobulins. The compounds are useful as potentiators when administered concurrently with another immunosuppressive drug for immunosuppressive treatments as discussed above. A conventional immunosuppressant drug, such as those above, may thus be administered in an amount substantially less (e.g. 20% to 50% of the standard dose) than when the compound is administered alone. Alternatively, the invention compound and immunosuppressive drug are administered in amounts such that the resultant immunosuppression is greater than what would be expected or obtained from the sum of the effects obtained with the drug and invention compound used alone. Typically, the immunosuppressive drug and potentiator are administered at regular intervals over a time period of at least 2 weeks.

The compositions of the invention may also be administered in combination with a conventional anti-inflammatory drug (or drugs), where the drug or amount of drug administered is, by itself, ineffective to induce the appropriate suppression or inhibition of inflammation.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

IV. Anticancer Treatment

As shown in FIG. 1, a compound of structure I, 14-deoxy-14α-fluorotriptolide (designated PG763), was cytotoxic to Jurkat cells (see Example 2) in a dose-dependent manner, at concentrations comparable to those in similar assays using triptolide. The invention thus includes the use of the invention compounds as cytotoxic agents, particularly to treat cancers. As used herein, "cancer" refers to all types of cancer or neoplasm or malignant tumors found in mammals especially humans, including leukemias, sarcomas, carcinomas and melanoma.

The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs. The term "carcinoma" refers to a malignant new growth made up of epithelial cells tending to infiltrate the surrounding tissues and give rise to metastases.

Included, for example, are cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin, including malignant melanoma, and gastrointestinal tract), solid organs, the nervous system, e.g. glioma (see Y. X. Zhou et al., 2002), and musculoskeletal tissue. The compounds may be used for treatment of various cancer cell types, including, but not limited to, brain, including medulloblastoma, head and neck, breast, colon, small cell lung, large cell lung, thyroid, testicle, bladder, prostate, liver, kidney, pancreatic, esophogeal, stomach, ovarian, cervical or lymphoma tumors. Treatment of breast, colon, lung, and prostate tumors is particularly contemplated.

The compositions may be administered to a patient afflicted with cancer and/or leukemia by any conventional route of administration, as discussed above. The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

Antitumor activity in vivo of a particular composition can be evaluated by the use of established animal models, as described, for example, in Fidler et al., U.S. Pat. No. 6,620,843. Clinical doses and regimens are determined in accordance with methods known to clinicians, based on factors such as severity of disease and overall condition of the patient.

V. Other Indications

The compounds of the present invention may also be used in the treatment of certain CNS diseases. Glutamate fulfills numerous physiological functions, including an important role in the pathophysiology of various neurological and psychiatric diseases. Glutamate excitotoxicity and neurotoxicity have been implicated in hypoxia, ischemia and trauma, as well as in chronic neurodegenerative or neurometabolic diseases, Alzheimer's dementia, Huntington's disease and Parkinson's disease. In view of the reported neuroprotective effects of triptolide, particularly protection from glutamate-induced cell death (Q. He et al., 2003; X. Wang et al., 2003), compounds of the invention are envisioned to antagonize the neurotoxic action of glutamates and thus may be a novel therapy for such diseases.

Recent evidence from MS patients in relapse suggests an altered glutamate homeostasis in the brain. Neurotoxic events occurring in MS patients can be responsible for oligodendrocyte and neuronal cell death. Antagonizing glutamate receptor-mediated excitotoxicity by treatment with compounds of this invention may have therapeutic implications in MS patients. Other CNS diseases such as Guillain-Barre syndrome, Meniere's disease, polyneuritis, multiple neuritis, mononeuritis and radiculopathy may also be treated with the compounds of the present invention.

The compounds of the present invention may also be used in the treatment of certain lung diseases. Idiopathic pulmonary fibrosis (PF) is a progressive interstitial lung disease with no known etiology. PF is characterized by excessive deposition of intracellular matrix and collagen in the lung interstitium and gradual replacement of the alveoli by scar tissue as a result of inflammation and fibrosis. As the disease progresses, the increase in scar tissue interferes with the ability to transfer oxygen from the lungs to the bloodstream. A 14-succinimide ester of triptolide has been reported to block bleomycin-induced PF (G. Krishna et al., 2001). Accordingly, the compounds of the present invention may be useful for treatment of PF. Treatment of other respiratory diseases, such as sarcoidosis, fibroid lung, and idiopathic interstitial pneumonia is also considered. Other diseases involving the lung and envisioned to be treatable by compounds of this invention include Severe Acute Respiratory Syndrome (SARS) and acute respiratory distress syndrome (ARDS). In particular, with respect to SARS, the reduction of virus content (SARS-CoV) before the peak of the disease process and the usefulness of corticosteroid treatment, as noted below, suggest that the development of the most severe, life-threatening effects of SARS may result from the exaggerated response of the body to the infection (immune hyperactivity) rather than effects of the virus itself (See also copending and co-owned U.S. provisional application Ser. No. 60/483,335, which is incorporated herein by reference.) Corticosteroid treatment has been used in SARS patients to suppress the massive release of cytokines that may characterize the immune hyperactive phase, in the hope that it will stop the progression of pulmonary disease in the next phase. Corticosteroid treatment has produced good clinical results in reduction of some of the major symptoms of SARS. However, there are several treatment-related side effects, and there is a clear need for more selective immunosuppressive and/or anti-inflammatory agents.

EXAMPLES

The following examples are intended to illustrate but not in any way limit the invention.

Example 1

Preparation of 14-deoxy-14α-fluorotriptolide

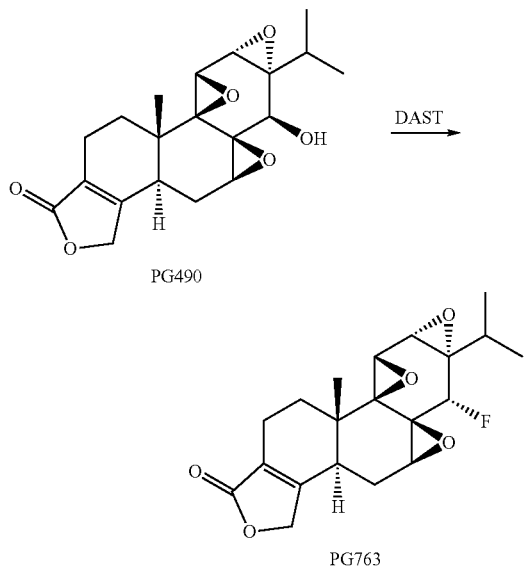

To a solution of PG490 (triptolide, 17.3 mg, 0.048 mmol) in dichloromethane (1.0 ml) at 0° C. was added (diethylamino)sulfur trifluoride (DAST, 100 μl, 0.763 mmol) under $N_2$. The reaction mixture was stirred at 0° C. for 2 hrs, and saturated $NaHCO_3$ solution (0.8 ml) was then added. The reaction mixture was extracted with 3×2 ml of dichloromethane. The combined organic layer was dried over anhydrous $NaSO_4$ and concentrated under vacuum. The desired product (PG763) was obtained in quantitative yield.

Analytical TLC Rf=0.78 (ethyl acetate/hexanes/methanol 1:1:0.1). IR (KBr): 3031.0, 2961.2, 2942.4, 2873.8, 1764.6, 1680.9, 1449.3, 1438.3, 1172.2, 1098.1, 1074.5, 1057.0, 1047.1, 1034.2, 1018.2, 1005.6, 987.3, 972.3, 923.9, 909.0, 743.6, 586.0, 566.0, 539.8, 527.6 $cm^{-1}$. $^1$HNMR (300 MHz, $CDCl_3$): δ=5.16 (d, 1H, 14-CH), 4.70 (q, 2H, 19-$CH_2$), 3.80 (d, 1H, 11-CH), 3.73 (d, 1H, 7-CH), 3.50 (t, 1H, 12-CH), 2.70 (m, 1H, 5-CH), 2.34 (d, 1H, 2-CHb), 2.27-2.02 (m, 3H, 6-CHb, 2-CHa and 15-CH), 1.95 (m, 1H, 6-CHa), 1.56 (dd, 1H, 1-CHb), 1.24 (m, 1H, 1-CHa), 1.11 (s, 3H, 20-$CH_3$), 1.10 (d, 3H, 17-$CH_3$), 0.91 (d, 3H, 16-$CH_3$) ppm.

Example 2

Cytotoxicity (MTT) Assay

Test compounds were dissolved in DMSO at a concentration of 20 mM. Further dilutions were done in RPMI 1640 medium (GIBCO, Rockville, Md.) supplemented with 10% Fetal Calf Serum (HyClone Laboratories, Logan, Utah).

Cytotoxicity of the compounds was determined in a standard MTT assay using Cell Proliferation Kit I (#1 465 007, Roche Diagnostics, Mannheim, Germany). Briefly, human T cell lymphoma (Jurkat) cells (4×10⁵ per well) were cultured for 24 h, in 96-well tissue culture plates, in the presence of serial three-fold dilutions of test compounds or medium containing the same concentration of DMSO as in the test samples at each dilution point. The cultures were then supplemented with 10 μl/well MTT reagent for 4h and then with 0.1 ml/well solubilizing reagent for an additional 16 h. Optical density at 570 nm ($OD_{570}$) was measured on a ThermoScan™ microplate reader (Molecular Devices, Menlo Park, Calif.). The data is presented as $OD_{570}$ values versus concentration of the compounds. The results for PG763 (14-deoxy-14α-fluorotriptolide), compared with PG490 (triptolide) and a medium control, are given in FIG. 1.

Example 3

Annexin V Apoptosis Assays

Test samples were diluted to 1 mM in complete tissue culture medium (RPMI 1640 medium plus 5% heat-inactivated fetal calf serum, 1% HEPES, 1% pen/strep, 1% glutamine). Aliquots were placed in microculture plates and serial dilutions were prepared so that the final concentration would encompass the range of 2 to 6,000 nM with half-log increments. Cells from an exponentially expanding culture of the Jurkat human T lymphoma cell line (#TIB-152 obtained from American Type Culture Collection, Manassas, Va.) were harvested, washed once by centrifugation, re-suspended in complete tissue culture medium, and further diluted to a concentration of 1×10⁶ cells/ml. A volume of 100 μl of the cells (1×10⁵ cells) was added to wells containing 100 μl of the diluted compounds, and the plates were incubated at 37° C. in a 5% $CO_2$ incubator.

After 24 hours, the plates were centrifuged to pellet the cells, and the cells were washed twice with 2% heat-inactivated fetal calf serum in PBS. To each well, 500 ul of binding buffer was added, according to the Annexin V assay procedure (BioVision, Inc., Mountain View, Calif.). Next, 5 μl of the fluorescein isothiocyanate (FITC) conjugate of Annexin V (BioVision, Inc.) was added to each well, followed by 5 minutes of incubation in the dark. In some assays, propidium iodide (BioVision, Inc.) was added at this stage to check for necrotic cells. The contents of the wells were individually transferred into test tubes, and apoptosis was analyzed using a FACSCalibur flow cytometer (BD Immunocytometry Systems, San Jose, Calif.). Cells positive for Annexin V binding were considered to be apoptotic, and the data were calculated as percent apoptotic cells.

Data were plotted as the concentration of compound versus percent apoptotic cells. Comparative data for two 14-substituted triptolides, 14α-hydroxytriptolide (also referred to as epitriptolide; designated PG524) and 14β-(methylthio)methyltriptolide (designated PG691), compared with PG490 (triptolide), are given in FIGS. 3A-B.

Example 4

IL-2 Production Assay

Test samples were diluted to 1 mM in complete tissue culture medium. Aliquots were placed in microculture plates that had been coated with anti-CD3 antibody (used to stimulate the production of IL-2 by Jurkat cells), and serial dilutions were prepared so that the final concentration would encompass the range of 0.001 to 10,000 nM in log increments. Cells from an exponentially expanding culture of Jurkat human T cell line (#TIB-152 obtained from American Type Culture Collection, Manassas, Va.) were harvested, washed once by centrifugation, re-suspended in complete tissue culture medium, and diluted to a concentration of $2 \times 10^6$ cells/ml. A volume of 50 µl of Jurkat cells ($1 \times 10^5$ cells) was added to wells containing 100 µl of the diluted compounds, 50 µl of PMA (10 ng/ml) was added to each well, and the plates were incubated at 37° C. in a 5% $CO_2$ incubator. After 24 hours, the plates were centrifuged to pellet the cells, 150 µl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as pg/ml of IL-2.

The data were plotted as the concentration of compound versus IL-2 concentration. The results for PG763 (14-deoxy-14α-fluorotdptolide), compared with PG490 (triptolide) and a solvent control, are given in FIG. 2. Comparative data for other 14-substituted triptolides, 14α-hydroxytriptolide (also referred to as epitriptolide; designated PG524) and 14β-(methylthio)methyltriptolide (designated PG691), compared with PG490 (triptolide), are given in FIGS. 4A-B.

The invention claimed is:

1. A method of suppressing the production of IL-2 from a T cell, comprising contacting the cell with a compound having the structure I:

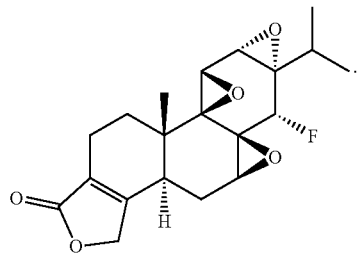

2. A method of inducing apoptosis in a cell, comprising contacting said cell with a compound having structure I:

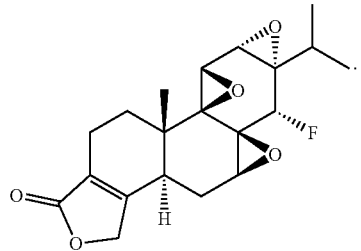

3. A method of decreasing the volume of a solid colon tumor in a subject, comprising administering to the subject an effective amount of a compound having structure I, wherein the compound is administered in a pharmaceutically acceptable vehicle:

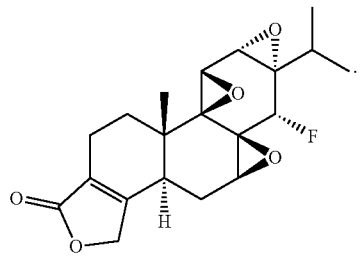

* * * * *